US010912673B2

(12) United States Patent
Khaderi et al.

(10) Patent No.: US 10,912,673 B2
(45) Date of Patent: Feb. 9, 2021

(54) METHODS AND SYSTEMS FOR TREATING INTRACRANIAL HYPERTENSION AND RELATED INDICATIONS USING AN OPTIC NERVE STENT OR SHUNT

(71) Applicants: Syed Khizer Rahim Khaderi, Venice, CA (US); Tsontcho Ianchulev, Harrison, NY (US)

(72) Inventors: Syed Khizer Rahim Khaderi, Venice, CA (US); Tsontcho Ianchulev, Harrison, NY (US)

(*) Notice: Subject to any disclaimer, the term of this patent is extended or adjusted under 35 U.S.C. 154(b) by 357 days.

(21) Appl. No.: 15/690,599

(22) Filed: Aug. 30, 2017

(65) Prior Publication Data

US 2018/0125707 A1 May 10, 2018

Related U.S. Application Data

(60) Provisional application No. 62/457,524, filed on Feb. 10, 2017, provisional application No. 62/443,931, (Continued)

(51) Int. Cl.
*A61F 9/00* (2006.01)
*A61F 9/007* (2006.01)
(Continued)

(52) U.S. Cl.
CPC .......... *A61F 9/007* (2013.01); *A61F 9/0017* (2013.01); *A61F 9/00781* (2013.01); (Continued)

(58) Field of Classification Search
CPC .... A61F 9/0017; A61F 9/00781; A61F 9/007; A61F 2210/0014; A61F 2210/0076; A61F 2220/0008; A61M 27/006; A61M 39/06
See application file for complete search history.

(56) References Cited

U.S. PATENT DOCUMENTS 5,041,081 A 8/1991 Odrich
5,171,213 A 12/1992 Price, Jr.
(Continued)

FOREIGN PATENT DOCUMENTS

WO 2018044974 A1 3/2018

OTHER PUBLICATIONS

International Search Report for PCT/US2017/049278, dated Dec. 1, 2017.
(Continued)

*Primary Examiner* — Philip R Wiest
(74) *Attorney, Agent, or Firm* — Novel IP

(57) ABSTRACT

Embodiments of the present specification provide surgical methods and apparatuses to deploy at least one stent through an optic nerve sheath in order to maintain an opening/fenestration for intracranial fluid egress. The surgical method creates a fenestration, an opening, a slit, or a hole, through an optic nerve sheath of a human patient. The fenestration is created in a minimally invasive manner using an applicator, such as an endoscopic visualization apparatus, that includes a stent or shunt for deploying through the fenestration. The presently disclosed specification is indicated to treat papilledema and/or intracranial hypertension and to deliver therapeutic compositions through the optic nerve sheath.

19 Claims, 10 Drawing Sheets

Related U.S. Application Data filed on Jan. 9, 2017, provisional application No. 62/381,608, filed on Aug. 31, 2016.

(51) Int. Cl.
*A61M 39/06* (2006.01)
*A61M 27/00* (2006.01)
A61B 5/03 (2006.01)
A61M 31/00 (2006.01)
A61M 39/02 (2006.01)
A61M 39/24 (2006.01)

(52) U.S. Cl.
CPC .......... *A61M 27/006* (2013.01); *A61M 39/06* (2013.01); *A61B 5/031* (2013.01); *A61F 2210/0014* (2013.01); *A61F 2210/0076* (2013.01); *A61F 2220/0008* (2013.01); *A61F 2230/0041* (2013.01); *A61F 2230/0043* (2013.01); *A61F 2250/0067* (2013.01); *A61F 2250/0068* (2013.01); *A61F 2250/0096* (2013.01); *A61F 2250/0097* (2013.01); *A61F 2250/0098* (2013.01); *A61M 31/002* (2013.01); *A61M 39/0247* (2013.01); *A61M 39/24* (2013.01); *A61M 2039/0205* (2013.01); *A61M 2039/027* (2013.01); *A61M 2205/04* (2013.01); *A61M 2205/3344* (2013.01)

(56) References Cited

U.S. PATENT DOCUMENTS

| | | | |
|---|---|---|---|
| 5,725,493 A | 3/1998 | Avery | |
| 5,817,075 A * | 10/1998 | Giungo | A61B 17/3468 604/294 |
| 6,514,238 B1 * | 2/2003 | Hughes | A61F 2/14 604/239 |
| 8,012,115 B2 * | 9/2011 | Karageozian | A61F 9/0017 604/264 |
| 9,168,172 B1 * | 10/2015 | Berdahl | A61F 9/00781 |
| 2004/0254517 A1 * | 12/2004 | Quiroz-Mercado | A61F 9/00781 604/8 |
| 2006/0200097 A1 | 9/2006 | Humayun | |
| 2006/0258994 A1 * | 11/2006 | Avery | A61F 9/0017 604/294 |
| 2012/0289883 A1 | 11/2012 | Meng | |

OTHER PUBLICATIONS

Written Opinion of the International Searching Authority for PCT/US2017/049278, dated Dec. 1, 2017.

* cited by examiner

METHODS AND SYSTEMS FOR TREATING INTRACRANIAL HYPERTENSION AND RELATED INDICATIONS USING AN OPTIC NERVE STENT OR SHUNT

CROSS-REFERENCE TO RELATED APPLICATIONS

The present application specification relies on, for priority, U.S. Patent Provisional Application No. 62/381,608, entitled "Methods and Systems for Treating Intracranial Hypertension and Related Indications Using An Optic Nerve Stent or Shunt", and filed on Aug. 31, 2016; U.S. Patent Provisional Application No. 62/443,931, entitled "Methods and Systems for Treating Intracranial Hypertension and Related Indications Using An Optic Nerve Stent or Shunt", and filed on Jan. 9, 2017; and U.S. Patent Provisional Application No. 62/457,524, entitled "Methods and Systems for Treating Intracranial Hypertension and Related Indications Using An Optic Nerve Stent or Shunt", and filed on Feb. 10, 2017.

The above-mentioned applications are herein incorporated by reference in their entirety.

FIELD

The present specification generally relates to methods and devices for treatment of intracranial pressure, and particularly to a microsurgical stent-type devices and associated methods for treatment of intracranial pressure.

BACKGROUND

Intracranial Hypertension (IH) relates to a neurological disorder that is characterized by increased intracranial pressure (ICP) arising from fluid pressure around the brain. The condition occurs when the pressure of the cerebrospinal fluid in the subarachnoid space (SAS), which is the space between the brain and the skull, increases above a normal range. Prolonged exposure to this condition often results in optic disc swelling, also known as papilledema, and subsequent damage to the optic disc, leading to a loss of vision.

While, in some patients, IH can be treated medically with the use of an ICP lowering agent such as acetazolamide and a weight-reduction program, surgical treatment is warranted for those patients who are experiencing vision loss, cannot tolerate medical therapy and/or develop progressive symptoms despite maximal medical treatment. Specifically, patients who cannot tolerate medical therapy or develop progressive symptoms despite maximal medical treatment undergo cerebrospinal fluid diversion procedures.

For those patients who are receiving maximal medical therapy and yet have progressive visual loss or impending visual loss with minimal or tolerable headaches, an optic nerve sheath fenestration (ONSF) procedure is warranted. ONSF releases the build-up of intracranial fluid and lowers intracranial pressure by providing an outflow window through the optic nerve sheath. It is believed that an opening within the optic nerve sheath will allow for a sudden and sustained drop in the SAS pressure and relief of edema in and around the optic nerve head and optic disc. The fenestration is done by accessing the retrobulbar section of the optic nerve and creating a slit in the sheath.

The three conventional surgical approaches for ONSF are superior eyelid, lateral orbital, and medial transconjunctival.

Superior Eyelid Approach:

The medial intraconal space is accessed through a superomedial eyelid crease incision. The orbital septum is opened and the medial horn of the levator aponeurosis is pushed laterally. With blunt dissection, a plane is created between the medial rectus muscle and the superior oblique tendon to access the posterior orbit avoiding the superior ophthalmic vein and vortex veins. With further posterior dissection, the optic nerve comes into view and a slit or rectangular window is created within the optic nerve sheath. Limitations of this approach include an increased distance from incision site to the optic nerve and an external (skin) incision.

Lateral Orbital Approach:

The procedure begins with an en bloc removal of the lateral orbital wall. The periorbita is incised in a T-shaped fashion and blunt dissection of the perimuscular fascial sheaths is performed until the lateral rectus muscle is identified. A traction suture is placed under the insertion of the lateral rectus muscle and the suture is anchored medially, adducting the eye in order to move the optic nerve laterally. Dissection with specially designed orbital-neurosurgical brain retractors is used to gain access to the optic nerve. Once the retrobulbar portion of the optic nerve is adequately exposed, an operating microscope is used to assist in a window incision of the optic nerve sheath. The periorbita is closed with interrupted sutures and the bone fragment is re-approximated to the lateral orbital wall using a nonabsorbable suture. Limitations of this approach include longer operating time, an external incision, and a more complex surgical procedure that requires removal of the orbital rim.

Medial Transconjunctival Approach:

A medial limbal conjunctival peritomy is performed and the conjunctiva incision is extended superiorly and inferiorly. The medial rectus muscle is isolated and the tendon is secured with a double armed 6-0 vicryl suture. The muscle is detached from the globe using scissors, leaving a small remnant of muscle tendon attached to the globe. A 5-0 Dacron traction suture is placed through the muscle tendon, and the globe is retracted laterally. The long posterior ciliary arteries are then identified between the superior and inferior poles of the insertion of the medial rectus muscle. With the aid of small malleable retractors the retrobulbar optic nerve is approached through the posterior reflection of Tenon's capsule and retrobulbar orbital fat. The orbital fat is retracted away from the optic nerve with small strips of cottonoids. A small angled forceps is used to improve exposure of the optic nerve. With the assistance of the operating microscope a sharp blade on a long handle is used to incise the optic nerve sheath approximately 2 mm posterior to the globe with careful attention to avoid any blood vessels on the surface of the nerve. A fine toothed forceps is inserted into the incision site and extended posteriorly with microscissors to a total length of 3-5 mm. A tenotomy hook may be inserted into the SAS and moved in the anterior-posterior direction to lyse any arachnoidal trabeculations and adhesions. On completion of the fenestration, the traction suture is removed, and the medial rectus is reattached to the globe using standard strabismus muscle technique. The conjunctiva is closed with 8-0 vicryl sutures. An antibiotic-steroid ointment is applied to the eye and a protective shield is placed over the eye to prevent any direct external pressure.

Current procedures are not effective due to variability of the slit and the healing response which leads to closure and an increase in the pressure. It is believed that nearly 50% of the surgeries require revision in a few years. Furthermore, ONSF can be associated with both minor and profound ocular complications. In a review of the published literature, the complication rate of ONSF was found to range broadly between 4.8-45% with a mean of 12.9%. In the same review of 317 cases of ONSF, 13% of cases were deemed a failure, which was defined as progressive visual loss despite the surgery or need for reoperation. In addition, case reports have described patients with progressive visual loss after ONSF due to sustained elevated ICP.

Furthermore, existing methods of optic nerve decompression require complex and invasive surgical procedures that are further complicated by the lack of easy access to the optic nerve which is behind the globe and has minimal surgical exposure. The surgery is normally performed in the hospital operating room and requires cutting vital ocular tissues including complete sectioning and subsequent reattachment of the muscles of the eye to expose and visualize the optic nerve sheath.

What is needed is an approach to optic nerve fenestration that is not surgically complex, avoids an external (skin) incision, and safely provides for the on-going release of intracranial fluid and/or on-going lowering of intracranial pressure and for deliverance of a therapeutic agent in the CSF and/or subconjunctival space of a patient.

What is also needed are novel stents and/or shunts which are specially designed for this particular surgical approach and that, when implanted, achieve the on-going release of intracranial fluid and/or on-going decrease of intracranial pressure and for deliverance of a therapeutic agent in the CSF and/or subconjunctival space of a patient.

SUMMARY

The following embodiments and aspects thereof are described and illustrated in conjunction with systems, tools and methods, which are meant to be exemplary and illustrative, not limiting in scope.

The present specification discloses a surgical method for treating at least one of intracranial hypertension and papilledema in a patient, comprising: navigating an applier device along a curvature of an eye of the patient without removing a medial rectus muscle associated with said eye; injecting a viscoelastic between the sclera of said eye and a Tenon's capsule associated with said eye; inserting at least one stent into an optic nerve sheath associated with the eye; observing an amount of fluid egress from the at least one stent; and removing the viscoelastic.

Optionally, the method further comprises creating a conjunctival access behind said eye. Optionally, the method comprises performing at least one of a medial peritomy on said eye prior to injecting said viscoelastic and a conjunctival incision on said eye prior to injecting said viscoelastic. The medial peritomy may be performed in a direction from 12 o'clock to 6 o'clock. Optionally, the method comprises performing a conjunctival incision.

Optionally, the method further comprises dissecting bluntly to bare the sclera prior to injecting said viscoelastic. The dissecting may be performed with Westcott scissors.

Optionally, the method further comprises isolating the medial rectus muscle prior to injecting said viscoelastic.

Optionally, the method further comprises identifying an insertion site on an optic nerve associated with the eye. The insertion site may be at a distance of at least 1.5 mm from a globe of said eye. Optionally, the method comprises inserting the at least one stent at the insertion site, wherein said insertion site is at least 1.5 mm posterior to the optic nerve.

Optionally, the method comprises inserting the at least one stent having a length between 3 mm and 6 mm. The method may comprise inserting the at least one stent having a diameter of 6 mm or less.

Optionally, the at least one stent comprises material with properties that are a combination of one or more of: biodegradable, heparin-coated, non-ferromagnetic Titanium, polyamide, super-elastic, bio-compatible, an alloy of Nickel-Titanium, rigid, flexible, expandable, and non-expandable.

Optionally, the at least one stent has as an elongated tube. The at least one stent may have a flat structure.

Optionally, the at least one stent shaped is J shaped, wherein a longer side of the J-shaped stent is longitudinally placed within the optic nerve sheath, and the curved, shorter side maintains an opening to an outside of said optic nerve sheath.

Optionally, the at least one stent further comprises one or more sensors.

Optionally, the at least one stent further comprises one or more therapeutic compositions.

Optionally, the method further comprises inspecting the site of inserting for fluid egress.

Optionally, the method further comprises removing the viscoelastic by aspirating.

The present specification also discloses a method of lowering intracranial pressure of a patient by maintaining an opening for intracranial fluid egress through an optical sheath of the patient, the method comprising: creating a conjunctival access in the patient's eye; navigating an applier device along a curvature of an eye of the patient without removing a medial rectus muscle associated with said eye; inserting at least one stent into the optic nerve sheath associated with the eye by using the applier device; and monitoring an amount of fluid egress from the at least one stent lowering intracranial pressure to a desired value.

Optionally, the method further comprises injecting a viscoelastic between the sclera of said eye and a Tenon's capsule associated with said eye; and removing the viscoelastic after fluid egress from the at least one stent.

Optionally, the method further comprises injecting an irrigation fluid between the sclera of said eye and a Tenon's capsule associated with said eye.

Optionally, the shunt comprises at least one sensor located at an ingress tip of the shunt. The sensor may be a MEMS sensor configured to measure intracranial pressure and to monitor fluid flow rates.

Optionally, the applier device comprises a curved applier coupled with a handle portion for extending and retracting the curved applier, with a radius of curvature of the curved applier ranging from 3 mm to 50 mm for facilitating navigation along the curvature of the eye. The applier device may be an endoscopic device comprising one or more illumination elements, and at least one endoscopic viewing element for visualization.

The present specification also discloses a method of delivering a therapeutic agent into one of a cerebral spinal fluid (CSF) and a subconjunctival space of a patient via a drug delivery device implanted in an optic nerve sheath of the patient, the drug delivery device comprising at least a reservoir containing the therapeutic agent coupled with a one-way valve and an outlet tube, the method comprising: creating a conjunctival access in the patient's eye; navigating an applier device along a curvature of an eye of the patient without removing a medial rectus muscle associated with said eye; identifying the optic nerve and corresponding insertion site in said eye; inserting the drug delivery device into the identified insertion site in the optic nerve; and delivering the therapeutic agent from the reservoir into the insertion site via the outlet tube.

Optionally, the method further comprises injecting a viscoelastic between the sclera of said eye and a Tenon's capsule associated with said eye; and removing the viscoelastic after inserting the drug delivery device into the identified insertion site.

Optionally, the one-way valve comprises a flexible membrane folded to define a chamber therebetween, the membrane being coupled with the reservoir and the outlet tube for delivering the therapeutic agent from the reservoir into the outlet tube.

Optionally, the reservoir is one of: a refillable subconjunctival, subtenon, ocular and extra ocular reservoir, the reservoir being connected into an extended optic nerve subdural space of the patient and being re-fillable for a plurality of drug administrations.

Optionally, the outlet tube comprises a uni-directional valve for allowing the therapeutic agent to flow from the reservoir towards the patient's eye under low pressure gradient conditions, while preventing retrograde flow back towards the reservoir.

The present specification also discloses a drug delivery device for delivering a therapeutic agent into one of a cerebral spinal fluid (CSF) and a subconjunctival space of a patient, the drug delivery device comprising: a stent, wherein the stent has a lumen extending therethrough and is J shaped, wherein a longer side of the J-shaped stent is configured to be longitudinally placed within an optic nerve sheath of the patient, and wherein the curved, shorter side of the J-shaped stent maintains an opening to an outside of the optic nerve sheath; and a reservoir in fluid communication with the stent, wherein the reservoir contains the therapeutic agent and is coupled with an outlet tube via a one-way valve.

The stent may have a length between 3 mm and 6 mm.

The stent may have an outer diameter of 6 mm or less.

Optionally, the stent comprises material with properties that are a combination of one or more of: bio-degradable, heparin-coated, non-ferromagnetic Titanium, polyamide, super-elastic, bio-compatible, an alloy of Nickel-Titanium, rigid, flexible, expandable, and non-expandable.

Optionally, the stent comprises an elongated tube.

Optionally, the stent has a flat exterior structure.

Optionally, the one-way valve comprises a flexible membrane that is folded to define a chamber wherein the membrane is coupled with the reservoir and the outlet tube for delivering the therapeutic agent from the reservoir into the outlet tube.

Optionally, the reservoir is at least one of a refillable subconjunctival reservoir, subtenon reservoir, ocular reservoir and extra ocular reservoir wherein the reservoir is configured to be connected into an extended optic nerve subdural space of the patient and configured to be re-fillable for a plurality of drug administrations.

Optionally, the outlet tube comprises a unidirectional valve for allowing the therapeutic agent to flow from the reservoir towards the eye under low pressure gradient conditions, while preventing retrograde flow back towards the reservoir. The unidirectional valve may be in a wet-straw configuration wherein a proximal end of a lumen of the unidirectional valve that is coupled to the reservoir is broader than a distal end of the lumen delivering the therapeutic agent into the insertion site. The unidirectional valve may be made of TEFLON.

The present specification also discloses a drug delivery device for delivering a therapeutic agent into one of a cerebral spinal fluid (CSF) and a subconjunctival space of a patient, the drug delivery device comprising: a stent, wherein the stent has a lumen extending therethrough and is L shaped, wherein a longer side of the L-shaped stent is configured to be longitudinally placed within an optic nerve sheath of the patient, and wherein the curved, shorter side of the L-shaped stent maintains an opening to an outside of the optic nerve sheath; and a reservoir in fluid communication with the stent, wherein the reservoir contains the therapeutic agent and is coupled with an outlet tube via a one-way valve.

The stent may have a length between 3 mm and 6 mm.

The stent may have an outer diameter of 6 mm or less.

Optionally, the stent comprises material with properties that are a combination of one or more of: bio-degradable, heparin-coated, non-ferromagnetic Titanium, polyamide, super-elastic, bio-compatible, an alloy of Nickel-Titanium, rigid, flexible, expandable, and non-expandable.

Optionally, the one-way valve comprises a flexible membrane that is folded to define a chamber wherein the membrane is coupled with the reservoir and the outlet tube for delivering the therapeutic agent from the reservoir into the outlet tube.

The aforementioned and other embodiments of the present specification shall be described in greater depth in the drawings and detailed description provided below.

BRIEF DESCRIPTION OF THE DRAWINGS

These and other features and advantages of the present specification will be appreciated, as they become better understood by reference to the following detailed description when considered in connection with the accompanying drawings, wherein.

DETAILED DESCRIPTION

Figure 1A:
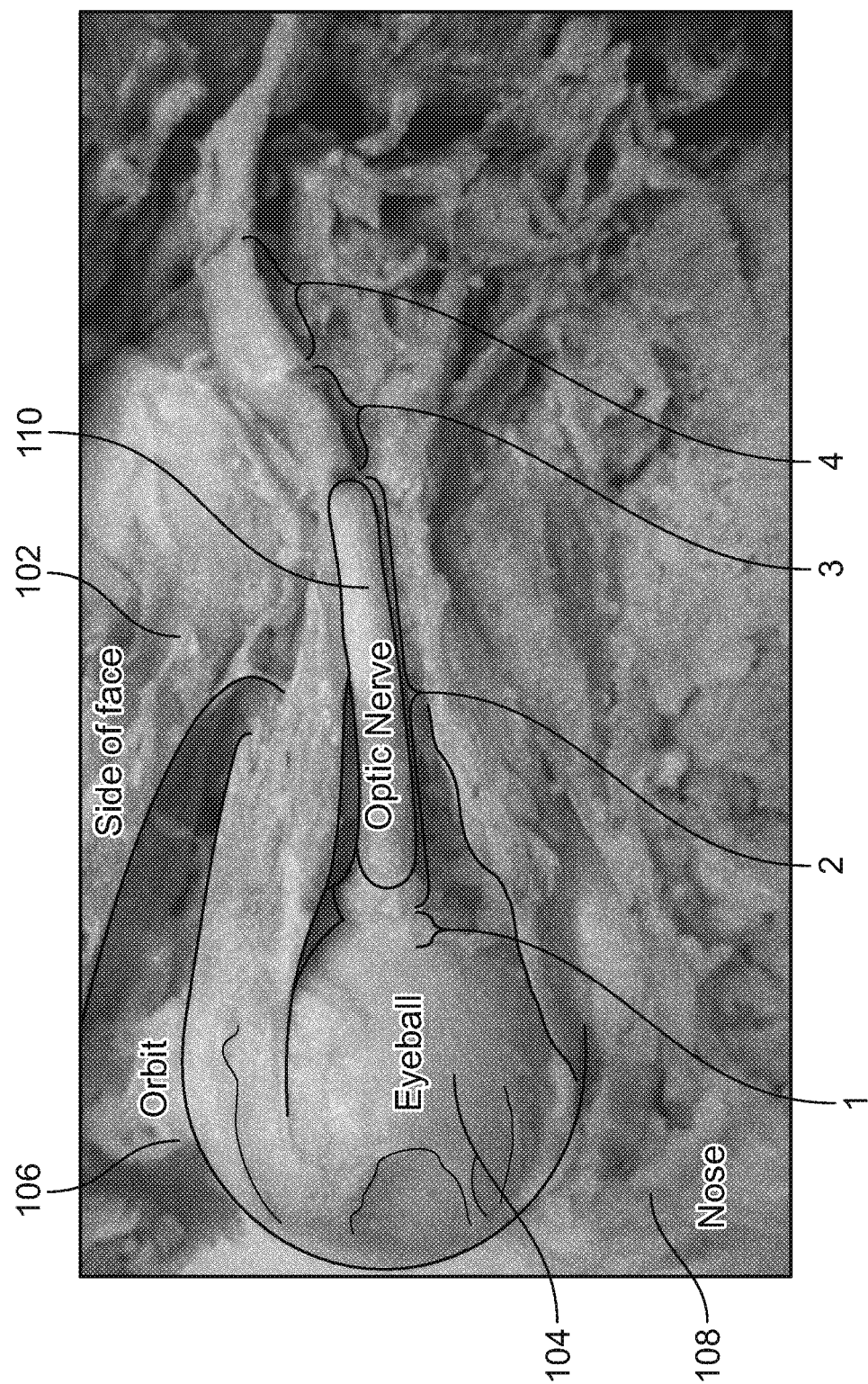
FIG. 1A illustrates a general layout of a region on the side of a face, and behind an eyeball of an eye in an orbit, as may be viewed from top while looking into orbit after top of the skull is removed.

In an embodiment, a surgical method and apparatus is provided to deploy at least one stent through an optic nerve sheath in order to maintain an opening for intracranial fluid egress. In an embodiment, the surgical method creates a fenestration, a slit, access point, cavity, or a hole (collectively "opening" or "fenestration") through an optical sheath of a human patient. The fenestration is created in a minimally invasive manner using an applicator, such as an endoscopic visualization apparatus, that includes a micro-stent or micro-shunt for deploying through the fenestration. In an embodiment, the applicator passes through the conjunctiva to access the retrobulbar space of the subject and implants the micro-stent through the optical sheath. In other embodiments, the applicator passes through Tenon's, or any other part within the anatomy of the eye that allows access to the retrobulbar space.

Intracranial pressure (ICP) refers to the pressure inside the skull and thus in brain tissue and cerebrospinal fluid (CSF). ICP is measured in millimeters of mercury (mmHg), centimeters of water/CSF (cm $H_2O$/CSF) or millimeters of water/CSF (mm $H_2O$/CSF) and, at rest, is normally 7-15 mmHg for a supine adult.

Intracranial hypertension, commonly abbreviated IH, IICP or raised ICP, refers to elevated pressure in the cranium. IH is defined as ICP >20 mm Hg (26 cm $H_2O$). At ICP of 20-25 mm Hg, the upper limit of normal, treatment to reduce ICP may be needed. It should be appreciated that there are slight deviations in normal pressure ranges and upper limits between adults and children, with the same being true regarding upper limits of normal and among people with larger body mass indexes (BMIs), depending on the disease or condition. For example, for Idiopathic Intracranial Hypertension, elevated lumbar puncture opening pressure is ≥250 mm $H_2O$/CSF in adults and ≥280 mm $H_2O$/CSF in children (250 mm $H_2O$/CSF if the child is not sedated and not obese) in a properly performed lumbar puncture.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention. In the description and claims of the application, each of the words "comprise" "include" and "have", and forms thereof, are not necessarily limited to members in a list with which the words may be associated.

It should be noted herein that any feature or component described in association with a specific embodiment may be used and implemented with any other embodiment unless clearly indicated otherwise.

FIG. 1A illustrates a general layout of a region on the side of a face 102, and behind an eyeball 104 of an eye in an orbit 106, as may be viewed from top while looking into orbit 106 after top of the skull is removed. Eyeball 104 is located just above nose 108. Eyeball 104 is connected to an optic nerve 110. The diameter of the optic nerve 110 increases from about 1.6 mm within eyeball 104 to 3.5 mm in orbit 106 to 4.5 mm within the cranial space. Optic nerve 110 component lengths are 1 mm in eyeball 104, 24 mm in orbit 106, 9 mm in the optic canal, and 16 mm in the cranial space before joining the optic chiasm. Partial decussation occurs in the optic chiasm, and about 53% of the fibers cross to form the optic tracts. Most of these fibers terminate in the lateral geniculate body. Based on this anatomy, optic nerve 110 may be divided in four parts as indicated in FIG. 1A and described in series, as it courses from eyeball 104 to an optic chiasm. The segments include: Optic Nerve Head (1), where optic nerve 110 begins in eyeball 104 with fibers from retina, Intraorbital Optic Nerve (2), the part of optic nerve 110 that lies within orbit 106, Intracanalicular Optic Nerve (3), the part within a bony canal known as the optic canal, and Intracranial Optic Nerve (4), the part within a cranial cavity, which ends at the optic chiasm.

The first segment of optic nerve 110 is the optic nerve head (ONH) located at the insertion of the nerve into the eye. The ONH represents the convergence of approximately 1.2 million axons of the retinal ganglion cells (RGCs). The ONH, which measures 1 mm in length and 1.5 mm in diameter, is represented by a physiologic blind spot on perimetry testing and is located approximately 4 mm nasal from the center of the macula (i.e. fovea). The ONH receives its blood supply from the circle of Zinn-Haller and the posterior ciliary arteries, which are branches of the ophthalmic artery.

The second segment of optic nerve 110 is the intraorbital optic nerve. At the ONH, the unmyelinated axons of a retinal nerve fiber layer (RNFL) make a 90° turn to exit the eye. The lamina cribrosa, a distinct region of the sclera consisting of stacks of fenestrated sheets of elastic fibers and connective tissue, allows the passage of the optic nerve axons from the eye into the retrobulbar orbital space. After passing through the lamina cribrosa, the axons become covered by myelin derived from oligodendrocytes. The presence of myelin increases the diameter of the intraorbital optic nerve to approximately 3 mm. Posterior to and continuous with the sclera, optic nerve 110 procures a dural sheath (of sheath 228), in addition to the arachnoid mater and pia mater. A unique anatomical feature of the intraorbital optic nerve is the fact that its length (28 mm) is nearly double the distance from the back of the eye to the orbital apex (15 mm). This configuration allows for the globe to freely rotate within the orbit and to compensate for any pathologic axial shifts within the orbit without causing visual dysfunction. The blood supply of the intraorbital optic nerve is derived from the pial network of vessels from the ophthalmic artery.

The intracanalicular optic nerve is the third segment of optic nerve 110, and begins at the point where optic nerve 110 enters the optic canal. At the orbital apex, the dura mater covering optic nerve 110 fuses with the periorbita of the orbit. It is also at this location that optic nerve 110 is encircled by the annulus of Zinn represented by the tendinous insertions of the four recti muscles. The intracanalicular portion of the optic nerve is anchored within the optic canal, which measures approximately 8-10 mm in length and 5-7 mm in width. The intracanalicular optic nerve represents a watershed zone because it has a dual vascular supply, anteriorly from branches of the ophthalmic artery and posteriorly from small vessels arising from the internal carotid artery and the superior hypophyseal artery.

The fourth segment of optic nerve 110 is the intracranial optic nerve. Optic nerve 110 enters the cranial vault underneath the anterior clinoid process and over the ophthalmic artery. Upon exiting the optic canal, the dura of the optic nerve fuses with the periosteum of the middle cranial fossa. The nerve then travels a variable distance, ranging from 8-12 mm, before joining the optic chiasm. The intracranial optic nerve is supplied by branches from the internal carotid artery, the superior hypophyseal artery, anterior cerebral artery, and anterior communicating artery.

Figure 1B:
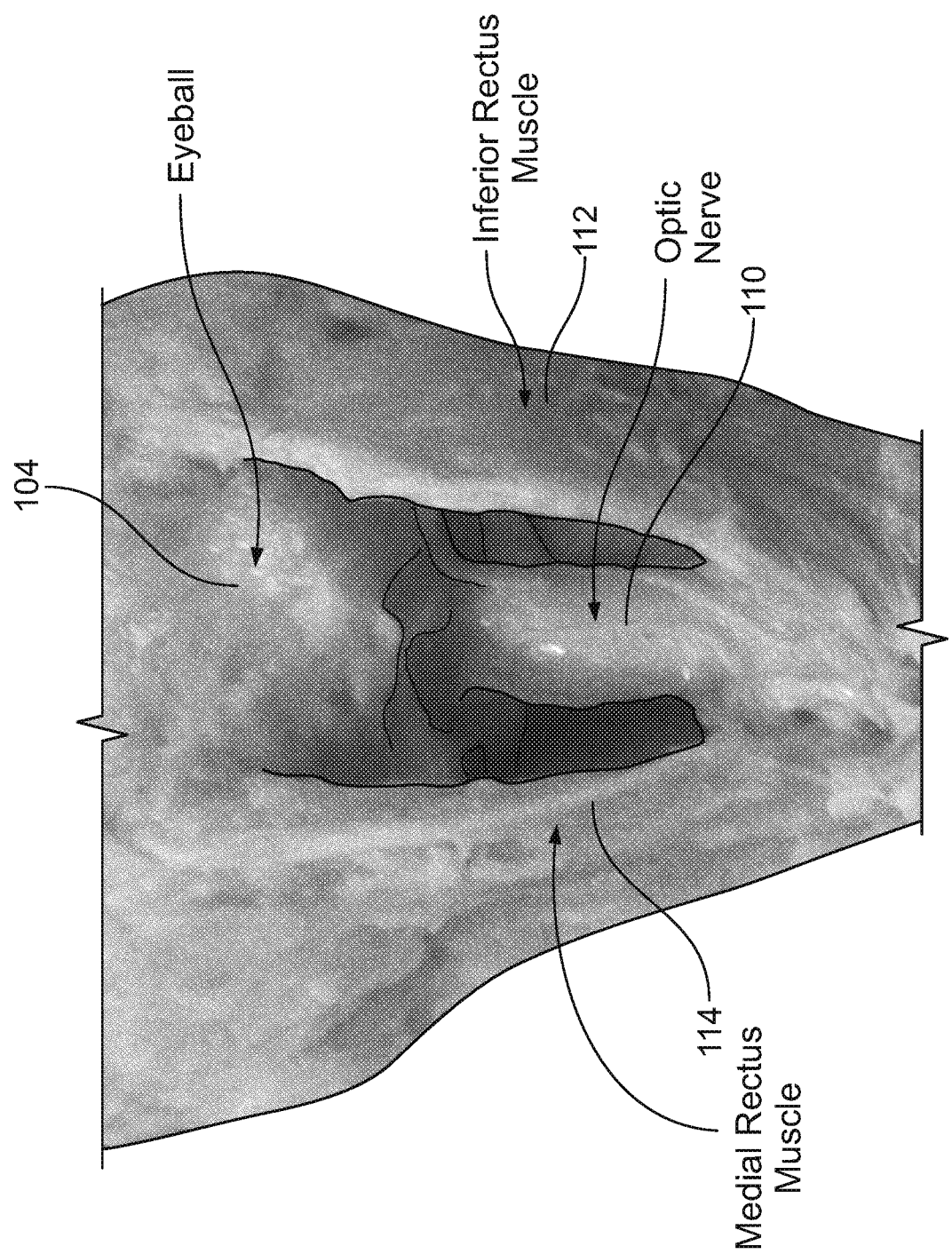
FIG. 1B illustrates another view of eyeball connected to optic nerve.

FIG. 1B illustrates another view of eyeball 104 connected to optic nerve 110. In the figure, optic nerve 110 is seen travelling between at least two muscles in orbit 106—an inferior rectus muscle 112 and a medial rectus muscle 114.

Figure 2:
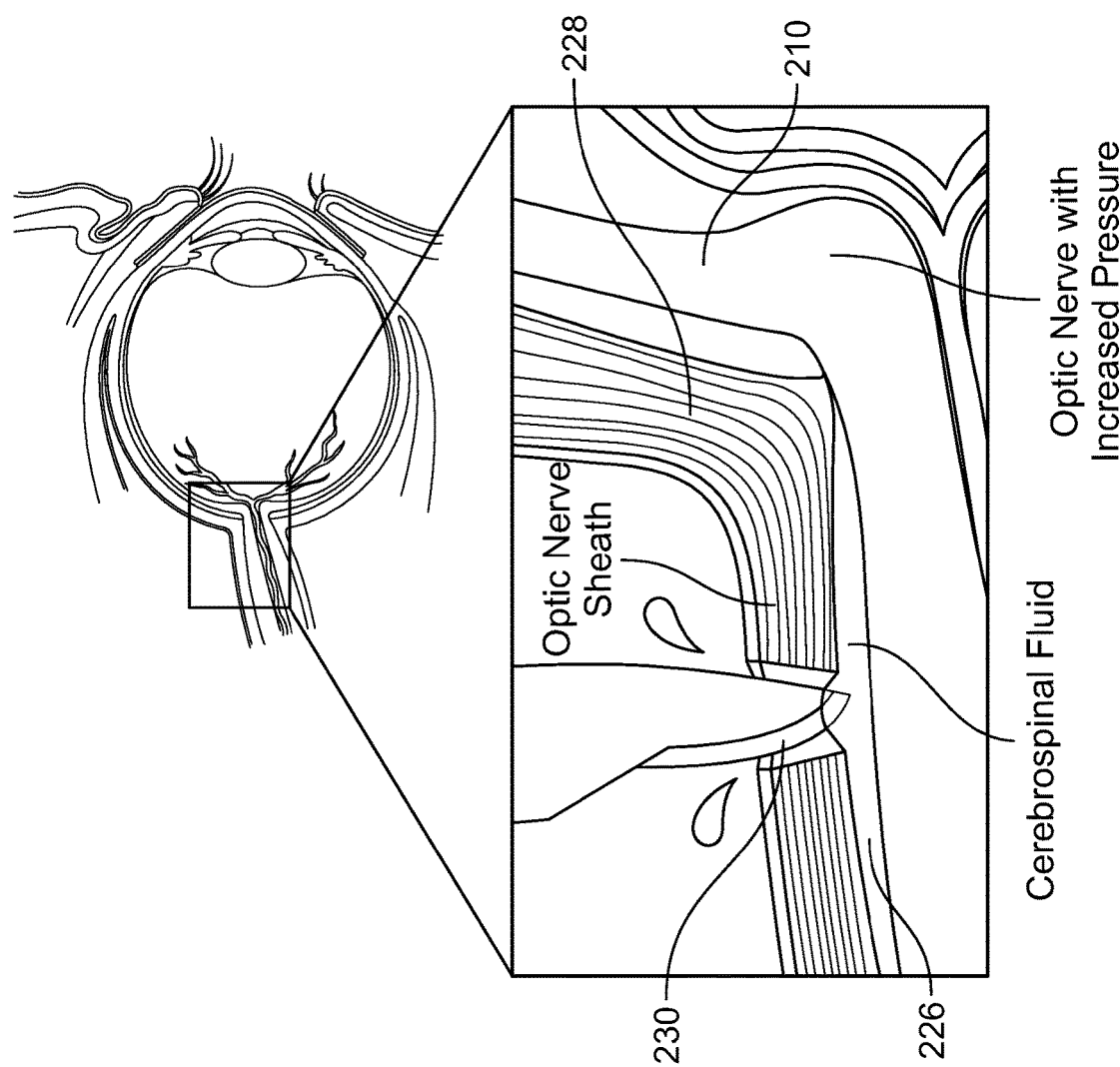
FIG. 2 illustrates a general layout of a region behind the globe of the eye that includes an optic nerve.

FIG. 2 illustrates a general layout of a region behind globe of the eye that includes an optic nerve 210. In the figure, optic nerve 210 is shown under elevated pressure resulting from increase in pressure of cerebrospinal fluid 226. An optic nerve sheath 228 is a layer of tissue that closely envelopes optic nerve 210 such that cerebrospinal fluid 226 occupies the space between optic nerve 210 and sheath 228. Optic sheath 228 includes three meningeal membranes—dura mater, arachnoid mater, and pia mater—that cover optic nerve 210.

Optic nerve 210 is a central nervous system (CNS) white matter tract. As a result of this common lineage between optic nerve 210 and the CNS, the SAS of optic nerve 210 is contiguous with the SAS of the brain. The arachnoid membrane of optic nerve 210, which functions to support and protect the underlying axons, is continuous with the arachnoid membrane of the subdural intracranial space and allows for the free circulation of cerebrospinal fluid (CSF) 226 around optic nerve 210 and brain.

By virtue of the fact that optic nerve sheath 228 serves as a CSF conduit between the brain and the eye, pathology involving the contents of the cranium can lead to pathology of the ONH. As discussed above, CNS pathology may be characterized by increased ICP, including intracranial masses, infectious diseases, inflammatory diseases, and IH, can impact the ONH, both structurally and functionally. When raised ICP is transmitted to the SAS within optic nerve sheath 228, ONH edema ensues, with papilledema being the first ophthalmoscopic sign of raised ICP. Investigations examining the pathophysiology of papilledema have shown axonal swelling at the ONH. Nerve fiber dysfunction due to axonal swelling can result in loss of central vision, a decrease in peripheral vision, and, ultimately, optic atrophy.

Accordingly, in accordance with another aspect, a plurality of drugs may be delivered to the CSF/brain through the optic nerve sheath using an implantable drug delivery device, particularly where antibiotics, biologics, and other therapeutics may otherwise have a low brain bioavailability when administered orally (PO) or intravenously (IV). Treatments of conditions/diseases, through CSF delivery of therapeutics, comprise hematologic/oncologic conditions, including primary tumors, secondary tumors, metastasis or inflammatory conditions that require drug deliver via cerebral spinal fluid.

Surgical Method for Treatment of IH

In one embodiment, the presently disclosed methods and systems relieve edema in and around the optic nerve head by creating a cerebrospinal fluid filter from the SAS of the optic nerve into the surrounding orbital tissue, thereby reducing the cerebrospinal fluid volume and pressure surrounding the optic nerve head. In another embodiment, the presently disclosed methods and systems increase a velocity of cerebrospinal fluid in the optic nerve sheath, thereby leading to a decrease in cerebrospinal fluid pressure communicated to the optic nerve head. In another embodiment, the presently disclosed methods and systems promote increased fibrous tissue proliferation at the incisional site, thereby preventing the transmission of elevated cerebrospinal fluid pressure to the optic nerve head. In various embodiments the method described in the present specification may be used for treating diseases/conditions such as but not limited to primary and secondary CNS malignancies, primary and secondary CNS bacterial and non-bacterial infections, and autoimmune diseases which require immunosuppressive therapy.

The method of the present specification may also be used to treat conditions related to elevated intracranial pressure, including but not limited to, idiopathic intracranial hypertension (IIH), higher elevations/space travel induced vision impairment and intracranial pressure (VIIP), and intracranial space occupying lesions such as but not limited to tumor, blood, foreign body, swelling, inflammation, and infection. In various embodiments, the method of the present specification may also be used to treat conditions related to elevated intraocular pressure, including but not limited to, primary open angle glaucoma, normal tension, and low tension glaucoma, ocular hypertension, primary closed angle glaucoma, secondary angle closure glaucoma related to neo-vascular glaucoma, pigment dispersion syndrome, and uveitic glaucoma.

In an embodiment a surgical method is provided for deploying at least one stent within an optic nerve sheath of a subject in order to treat Intracranial Hypertension (IH), relieve optic disc swelling, or otherwise treating papilledema.

Figure 3A:
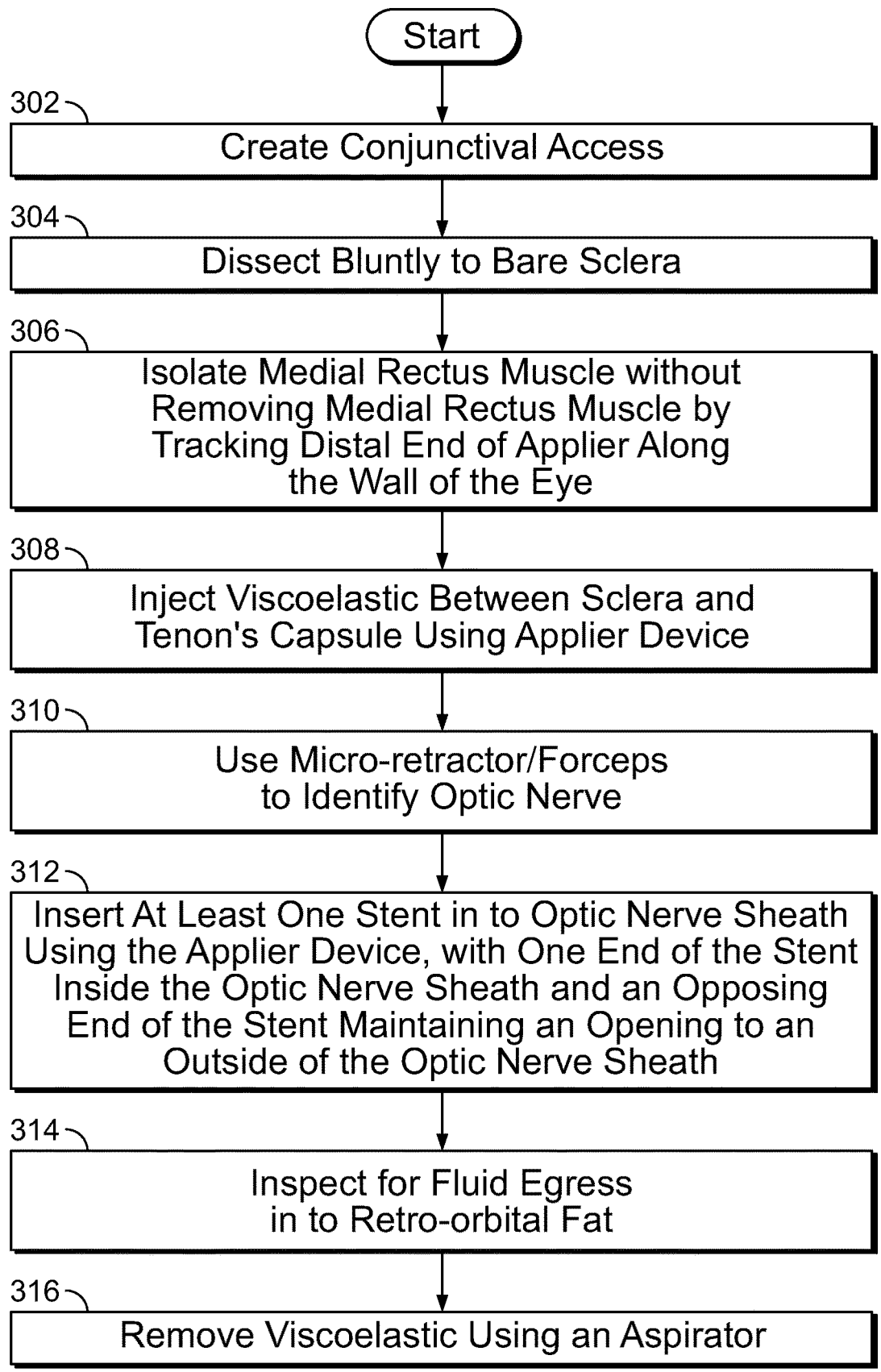
FIG. 3A illustrates an exemplary process for implanting a shunt or stent in the optic nerve sheath.

FIG. 3A is a flow chart that describes a surgical process in accordance with an embodiment of the present specification. At 302, a conjunctival access is created. In an embodiment, a medial peritomy is performed in a direction of 12 to 6 'o clock. The peritomy involves a surgical incision of the conjunctiva and subconjunctival tissue about the circumference of a cornea. In another embodiment, a small conjunctival incision is performed, avoiding a full peritomy.

At 304, a blunt dissection is performed with Westcott scissors in order to bare sclera. Sclera is the tough, white outer coat of the eyeball, which covers approximately the posterior five-sixths of its surface, continuous anteriorly with the cornea and posteriorly with the external sheath of the optic nerve. At 306, the medial rectus (MR) muscle is isolated but, unlike the prior art, is preferably not removed or detached. Rather, a minimally invasive applier, such as an endoscope with optical visualization and a curved distal end, is used to track along the wall of the eye to reach the optic nerve without the need for a significant abduction or reversion of the eyeball and thereby not requiring the medial rectus muscle to be removed. In a less preferred embodiment, the MR muscle is detached from the globe using scissors, leaving a small remnant of muscle tendon attached to the globe. Such a detachment may facilitate further visualization, for example in cases where endoscopic approach is unavailable.

At 308, a viscoelastic is injected between sclera and Tenon's capsule. In embodiments, the viscoelastic functions as a spacer between the sclera and the Tenon's capsule. In embodiments, the viscoelastic also preserves vasculature during subsequent possible placement of an endoscope for visualization and navigation to a retro-orbital nerve. In alternative embodiments, a fluid may be infused or irrigated through the optic nerve sheath for gentle visco-dissection of the sheath without the injection of a viscoelastic material.

At 310, a micro dissecting retractor or forceps is used to identify the optic nerve. Additionally, an insertion site is identified on the optic nerve. In embodiments, a site at a distance of about 2 mm from the globe is identified for insertion. At 312, one or more stents (or shunts) are inserted in to the optic nerve sheath at the site identified in the previous step. In embodiments, the one or more stents are inserted at least 1 mm posterior to the optic nerve, preferably in the range of 1.5 mm to 3 mm. In an embodiment, the stents vary in length. In an embodiment, the length of stents may be between 3-6 mm. In accordance with an aspect, at 312 a depot stent-type drug delivery device is inserted in to the optic nerve sheath at the site identified in step 310.

At 314, an inspection is performed at the insertion site to check for fluid egress in to retro-orbital fat. In an embodiment, the surgical process is guided with fluorescence imaging to identify fluid flow, and therefore identify fluid egress in to the retro-orbital fat.

Subsequently, at 316, any viscoelastic is removed by aspiration with the use of a micro-aspiration unit.

Stent/Shunt

Figure 4A:
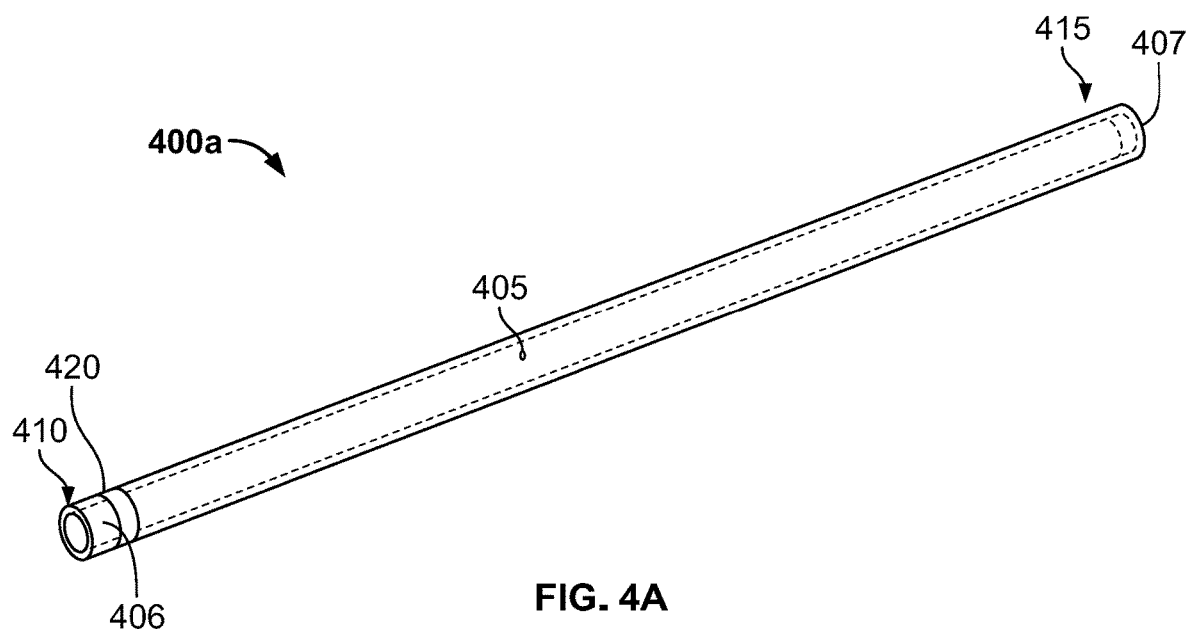
FIG. 4A is a perspective view of a stent or shunt, in accordance with an embodiment of the present specification.

FIG. 4A shows a stent or shunt 400a, in accordance with an embodiment of the present specification. In a preferred embodiment, the stent 500a shown in FIG. 4A is inserted in to the optic nerve sheath at the identified site as described at step 312 of FIG. 3A above. The stent or shunt 400a is an elongate member having a proximal end 410, a distal end 415, and at least one element or structure that permits fluid (such as aqueous humour) to flow along the length of the shunt 400a such as through the shunt 400a and/or around the shunt 400a. In accordance with aspects of the present specification, the stent or shunt 400a comprises at least one internal lumen 405 having at least one opening for ingress of fluid and at least one opening for egress of fluid. In the embodiment of FIG. 4A, the shunt 400a includes a single opening 406 at the proximal end 410 and a single opening 407 at the distal end 415 that both communicate with the internal lumen 405.

Figure 4B:
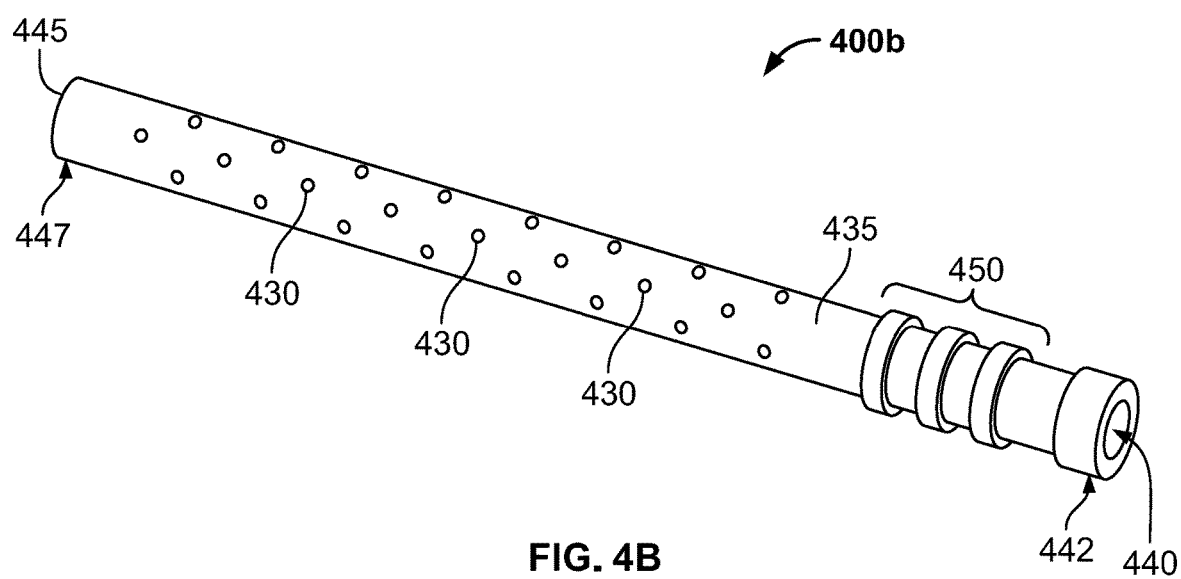
FIG. 4B is a perspective view of a stent or shunt, in accordance with another embodiment of the present specification.

FIG. 4B shows a stent or shunt 400b, in accordance with another embodiment of the present specification. In this embodiment, the stent or shunt 400b comprises a plurality of openings or pores 430 that communicate with an internal lumen 435. The internal lumen 435 runs along a length of the stent 400b from an opening 440 at a proximal end 442 to an opening 445 at a distal end 447. In this embodiment, the plurality of openings or pores 430 function as channels for flow of fluid in addition to the internal lumen 435. In alternate embodiments, the plurality of openings 430 may be configured as fenestrations, slits or slots, for example.

Referring now to FIGS. 4A and 4B simultaneously, the internal lumens 405, 435 serve as passageway for the flow of aqueous humour through the shunts 400a, 400b from an anterior chamber to a suprachoroidal space. In addition, the internal lumens 405, 435 are used to mount the shunts 400a, 400b onto a delivery system. The internal lumens 405, 435 can also be used as a pathway for flowing irrigation fluid into the eye generally for flushing or to maintain pressure in the anterior chamber. In the embodiments of FIGS. 4A, 4B the shunts 400a, 400b have a substantially uniform diameter along their entire lengths; however, in alternate embodiments, the diameter of the shunts can vary along its length.

Still alternately, although the shunts 400a, 400b are shown as having circular cross-sectional shapes, the shunts can have various cross-sectional shapes (such as, but not limited to, an oval, square or rectangular cross-sectional shape) and can vary in cross-sectional shape moving along their lengths. In some embodiments, as illustrated in the stent or shunt 400a, at least one positioning marker or aid 420 is provided, such as near the proximal end 410, to provide sensory feedback to the user for real-time placement of the shunt, confirmation of placement of the shunt and/or during patient follow-up post implantation of the shunt. In various embodiments, the marker or aid 420 may be visual, tomographic, echogenic, or radiopaque.

In some embodiments, as illustrated in the stent or shunt 400b, at least one retaining element 450 is provided, such as near the proximal end 442, to enable anchoring the implanted stent 400b. In various embodiments, the retaining element 450 comprises one or more retention elements such as, but not limited to, protrusions, ridges, rings, wings, tines, or prongs, that lodge into anatomy to retain the shunt in place (that is, to prevent migration of the shunt) and to ensure communication between the space below the optic nerve sheath and the retrobulbar space. In various embodiments, the retention elements comprise extension plates, pedicles, finger-extensions and other structures at the contact interface with the optic nerve. In some embodiments, the retaining element 450 is flexible or deformable and can be made from biocompatible materials such as, but not limited to, polyamide or silicone elastomer. In some embodiments, the retaining element 450 is stiff and made from materials such as, but not limited to, stainless steel or Nitinol. In various embodiments, the retaining element 450 vary in shape such as, but not limited to, barb-shaped, ring or round shaped, rectangular, triangular or any combinations thereof. It should be appreciated that in some embodiments a stent or stunt may comprise a combination of features such as marker 420, retaining element 450 and the plurality of pores 430.

In various embodiments, at least one stent or shunt (such as the stent 400a, 400b) of a length that may vary between 0.3 millimeters (mm) and 9 mm, is inserted in to the optic nerve sheath. In some embodiments, a stent or shunt has a length in a range of 2 mm to 7 mm. In embodiments, the stent or shunt outer diameter does not exceed the diameter range of a standard optical nerve, which is typically in a range of 5 to 6 mm. The stent or shunt may be inserted at a site that is at least 2 mm posterior to the optic nerve. In an embodiment, the stent or shunt has an elongated tubular structure that has flexibility and is relatively flat, such that its shape corresponds to that of the optical sheath that has a lumen. In an embodiment, the length of the stent embedded within an optic nerve sheath is less than or equal to 5 mm.

In an embodiment, the stent or shunt is J-shaped, L-shaped, or otherwise curved at one end, such that the longer side is longitudinally placed within the optic sheath and the curved, shorter side maintains an opening to the outside. In an embodiment, the stent's structure may include a long arm which extends parallel to the optic nerve under the sheath, and a curved end with an opening that goes through the sheath. In an embodiment, an external rim is placed around the opening at the curved end in order to prevent sinking/migration of the stent below the nerve sheath. In an embodiment, the stent is an expandable longitudinal element and/or memory shaped element comprising a mesh-like device which assumes a different shape or larger internal diameter upon deployment. In embodiments, retention rings, ridges, or other retention features may be provided with the stent, to keep it under the sheath. Additionally, a retention ring, a whisker, an extension, cap, or any other device may be provided outside the sheath to keep it from migrating fully into the optic nerve. In an embodiment, parts of the stent are fenestrated to aide in fluid flow.

In some embodiments, the stent or shunt is manufactured from a material that enables it to retain its size and shape permanently within the optic nerve sheath until it is surgically removed. In some embodiments, the stent or shunt is manufactured using a bio-degradable material while in alternate embodiments the stent or shunt is manufacture using a non-biodegradable material. In various embodiments, the stent or shunt can be made of various materials, such as, for example, polyamide, Nitinol, platinum, stainless steel, molybdenum, or any other suitable polymer, metal, metal alloy, or ceramic biocompatible material or combinations thereof.

In embodiments, non-ferrous materials are preferred, as they are safe for MRI (Magnetic Resonance Imaging) procedures. Other materials of manufacture or materials with which the shunt can be coated or manufactured entirely include Silicone, PTFE, ePTFE, differential fluoropolymer, FEP, FEP laminated into nodes of ePTFE, silver coatings (such as via a CVD process), gold, prolene/polyolefins, polypropylene, poly(methyl methacrylate) (PMMA), acrylic, Polyethylene Terephthalate (PET), Polyethylene (PE), PLLA, and parylene. The stent or shunt can be reinforced with polymer, Nitinol, or stainless steel braid or coiling or can be a co-extruded or laminated tube with one or more materials that provide acceptable flexibility and hoop strength for adequate lumen support and drainage through the lumen. The shunt can alternately be manufactured of nylon (polyamide), PEEK, polysulfone, polyamide-imides (PAI), polyether block amides (Pebax), polyurethanes, thermoplastic elastomers (Kraton, etc.), and liquid crystal polymers. In one embodiment, the stent or shunt is a heparin-coated, non-ferromagnetic titanium stent or shunt.

In embodiments, the stent or shunt can also be coated or layered with a material that expands outward once the shunt has been placed in the eye. The expanded material fills any voids that are positioned around the shunt. Such materials include, for example, hydrogels, foams, lyophilized collagen, or any material that gels, swells, or otherwise expands upon contact with body fluids.

In embodiments, the stent or shunt is an elongated tube or spacer, expandable or non-expandable, drug-eluting or non-drug eluting as may be required for the range of clinical applications, rigid or flexible. In embodiments, the stent or shunt may be used for delivering therapeutics. Along with retention features, the ability to expand as needed may ensure proper engagement of the stent or shunt in the tissue and create desired outflow tract. In an embodiment, the stent or shunt includes a valve. In embodiment, the stent or shunt is used to deliver antibiotics, biologics, and other therapeutics for CNS delivery that may otherwise have a low brain bioavailability when administered orally (PO) or through Intravenous (IV). Therapeutics positioned in a reservoir in the stent or shunt passively drains into a low pressure retrobulbar space.

In embodiments, the stent or shunt is optionally combined with one or more sensors. In some embodiments, one or more sensors are implanted without the stent or shunt. The optional sensors (with or without the stent or shunt) may be used to monitor flow rates, pressure, and other parameters that may be monitored from the location of the stent within the optic nerve sheath. In an embodiment, a micro sensor is implanted for eye pressure measurement, the micro sensor comprising a MEMS sensor or sensors with a power source that is not local to the sensor. Sensors may help monitoring the surgical procedure as well as may be deployed with the stent to monitor the subject regularly for pressure variations. The sensors may communicate with external handheld or other devices for transfer and analysis of measurement data. A smartphone-app may be integrated in the communication system to connect the patient, the doctor, a central database, or any other entity.

Figure 5A:
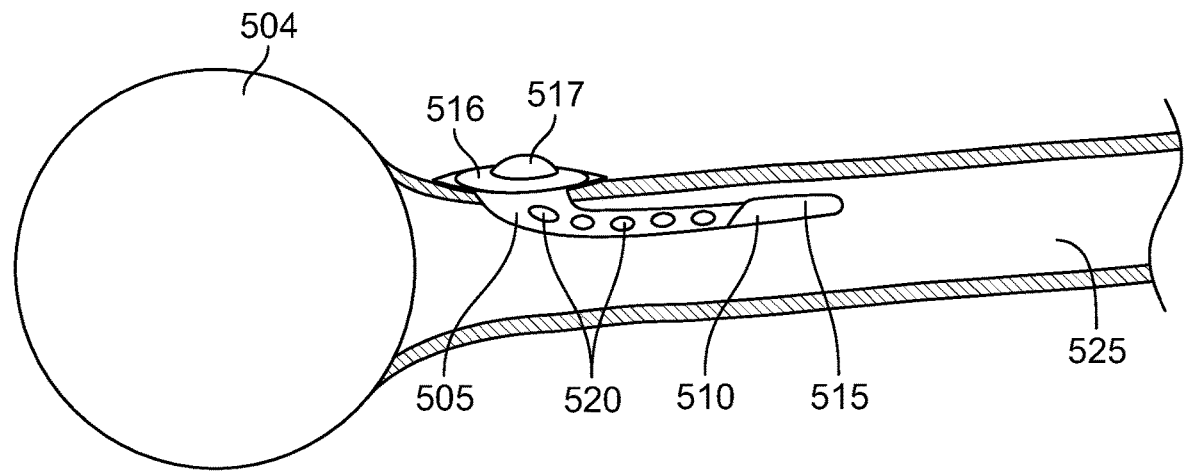
FIG. 5A illustrates a stent or shunt carrying an optional sensor and positioned within an optic nerve sheath, in accordance with an embodiment of the present specification.

FIG. 5A illustrates a stent or shunt 505 carrying an optional sensor 510 in accordance with an embodiment of the present specification. In FIG. 5A, an eyeball 504 is depicted with the stent or shunt 505 (the stent or shunts 400a, 400b of FIGS. 4A, 4B respectively) shown positioned within the optic nerve sheath 525. At least one sensor 510 is located at an ingress tip 515 of the stent or shunt 505 such that the at least one sensor 510 lies within the sheath 525—specifically, the subarachnoid space. In some embodiments, the at least one sensor 510 is a MEMS sensor configured to measure intracranial pressure and/or to monitor flow rates. The stent or shunt 505 enables fluid (such as aqueous humour) to flow from at least one opening at the ingress tip 515 to an egress tip 516 via at least one internal lumen along the length of the shunt 505. An opening 517 is included in the egress tip 516 and is in fluid communication with the internal lumen. In embodiments, additional fluid flow is enabled through a plurality of fenestrations or pores 520 that communicate with the internal lumen.

Figure 5B:
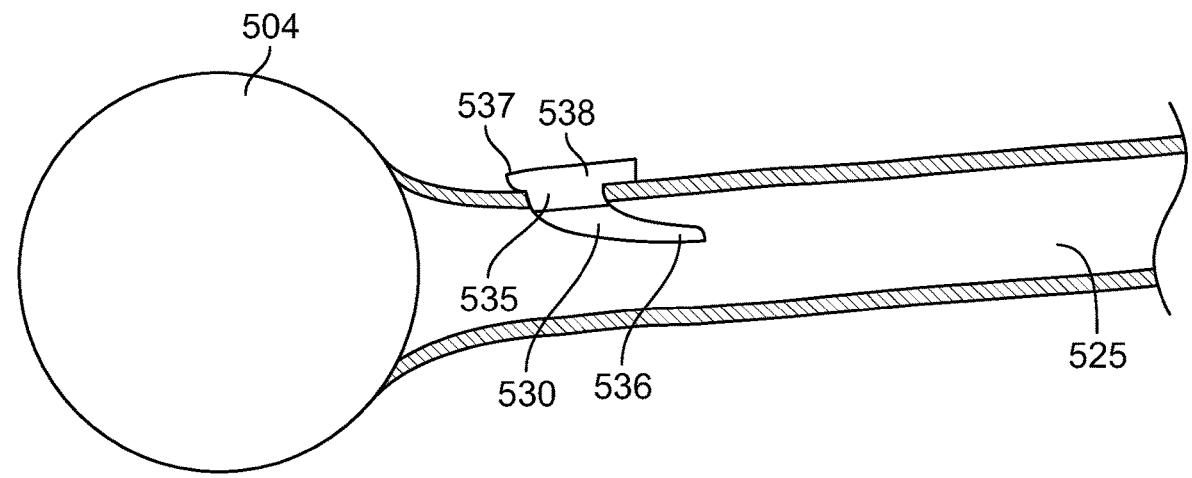
FIG. 5B illustrates a sensor positioned within the optic nerve sheath without a stent or shunt, in accordance with an embodiment of the present specification.

FIG. 5B illustrates an embodiment showing an eyeball 504 where a sensor 530 (without a stent or shunt) is positioned within the optic nerve sheath 525 so as to lie within the subarachnoid space. In embodiments, the sensor 530 is mounted on a first end 536 of a base member 535. The base member 535 comprises a retention feature 537, such as a collar, at a second end 538 to retain the base member 535 and hence the sensor 530 in position within the sheath 525.

Drug Delivery Method and Device

Figure 3B:
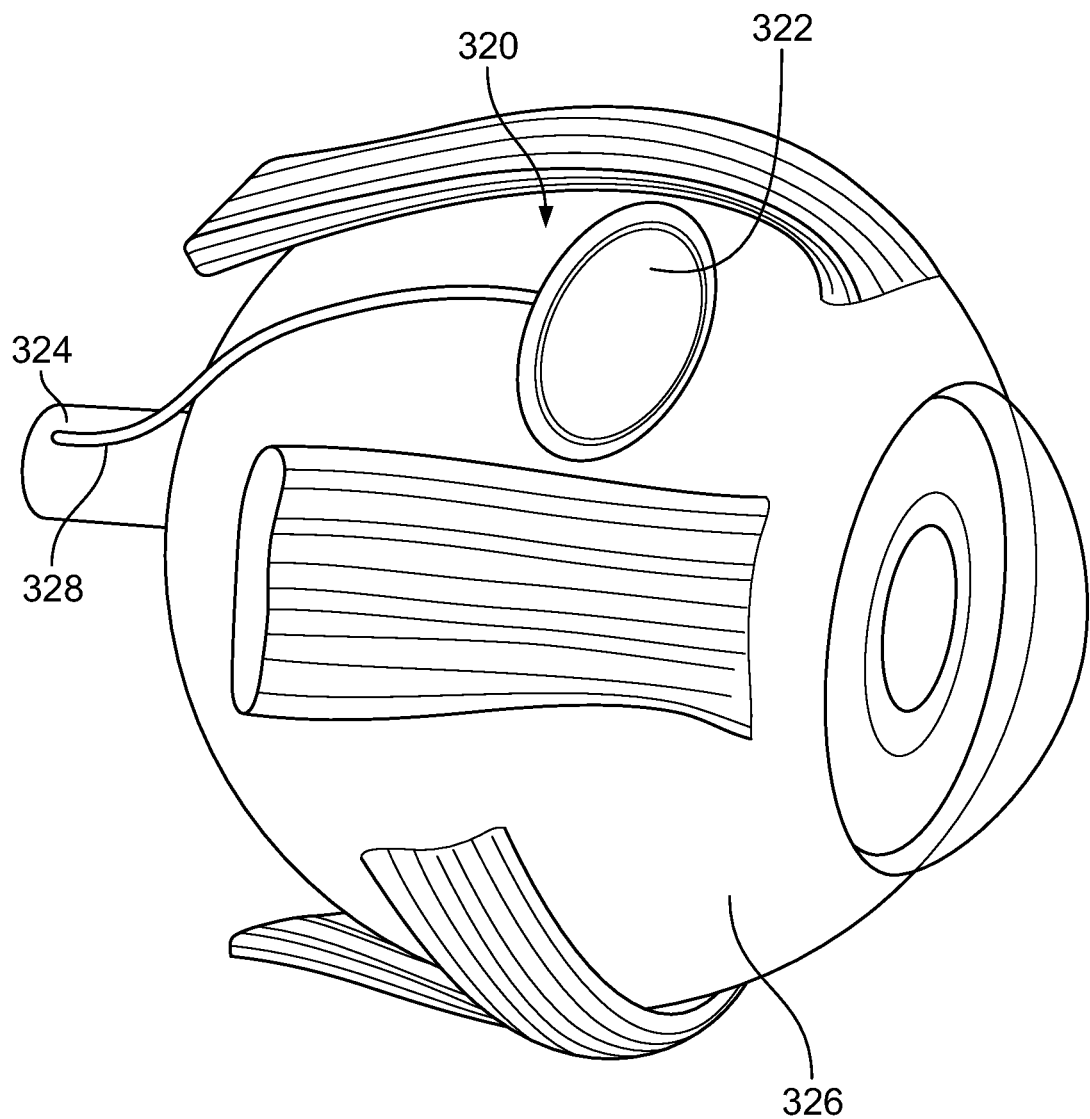
FIG. 3B illustrates a stent-type drug delivery device implanted into the optic nerve sheath, in accordance with an embodiment of the present specification.

Referring back to FIG. 3A, in accordance with another aspect of the present specification, at step 312 a depot stent-type drug delivery device is implanted in to the optic nerve sheath at the site identified in step 310. FIG. 3B illustrates a stent-type drug delivery device implanted into the optic nerve sheath, in accordance with an embodiment of the present specification. As shown, a depot stent-type drug delivery device 320 is a valved or flow-restrictive device that allows unidirectional flow of therapeutic drugs from a refillable reservoir 322 or chamber to the CSF 324 or a subconjunctival space of an eyeball 326 via an outlet tube 328 in fluid communication with the reservoir 322.

Figure 6A:
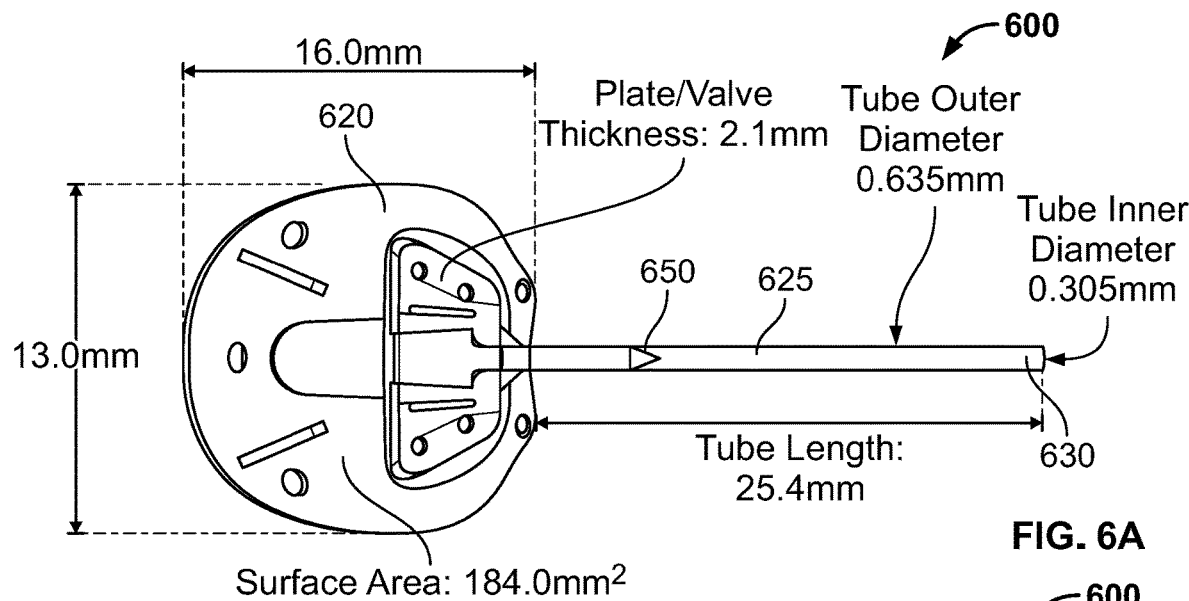
FIG. 6A shows a perspective view of an exemplary drug delivery device or valve in accordance with an embodiment of the present specification.
Figure 6B:
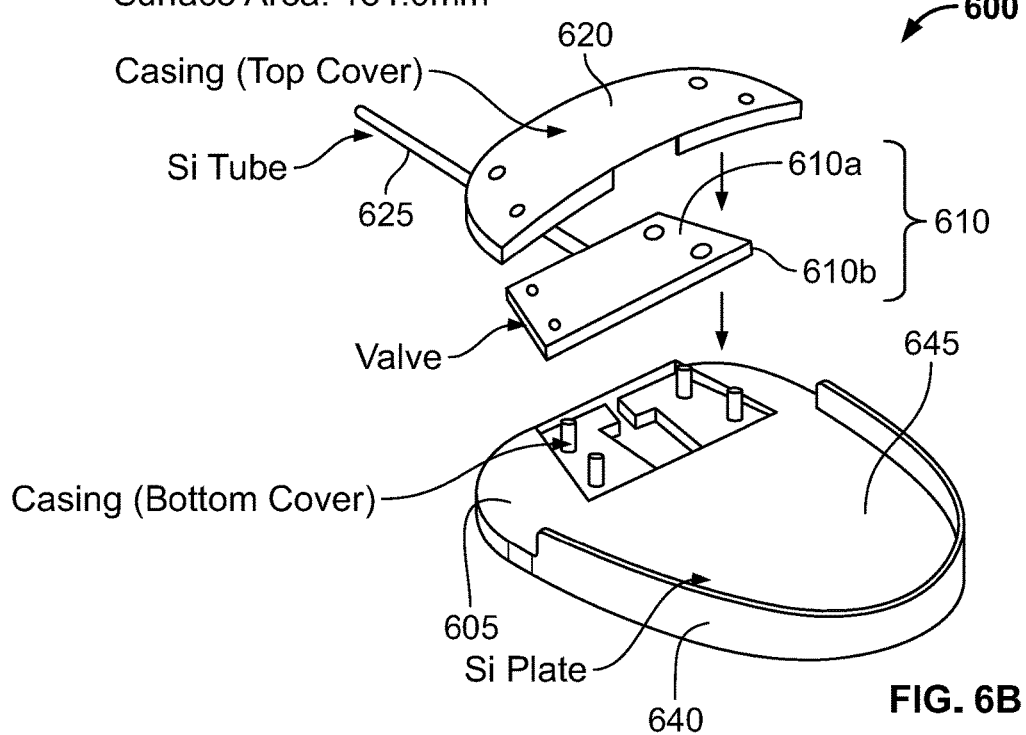
FIG. 6B is an exploded view of an exemplary drug delivery device of FIG. 6A, in accordance with an embodiment of the present specification.
Figure 6C:
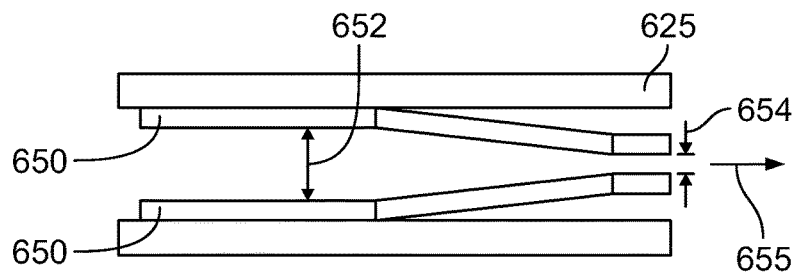
FIG. 6C is a cross-sectional illustration of an outlet tube of the drug delivery device of FIG. 6A including a unidirectional valve, in accordance with an embodiment of the present specification.

FIG. 6A shows a perspective view of a drug delivery device or valve 600 while FIG. 6B shows an exploded view of the device 600 in accordance with an embodiment. The device or valve 600 comprises a base plate 605, a flexible membrane 610 (such as that of siliconized rubber), a cover plate 620 and a flexible outlet tube 625 (such as that of siliconized rubber). The membrane 610 is folded to form a valve comprising a pair of membrane members 610a and 610b defining a chamber there-between. A rear portion of the base plate 605 is surrounded by a ridge 640 to form a reservoir 645 to store a prescribed quantity of drug. The membrane members 610a and 610b are placed between the plates 605, 620 and these plates are pressed together and interlocked to hold the membrane members in position. The outlet tube 625 (having a lumen) extends from the plates 605, 620 and the membrane 610 so that its free end 630 may deliver metered doses of the drug, stored in the reservoir 645, into the CSF. In embodiments, the reservoir 645 allows sustained release of at least one drug in a range from 1 to 360 days as therapeutically indicated. In accordance with aspects of the present specification, the reservoir 645 is a refillable subconjunctival, subtenon or other ocular/extra ocular reservoir that, in various embodiments, is connected into the extended optic nerve subdural space and can be charged or refilled for a plurality of drug administrations and dosing regimens. The reservoir 645 is either fixed or adjacent to the sclera for easy access to enable refills. In an embodiment, the reservoir has a capacity less than or equal to 700 mm$^3$ In accordance with aspects of the present specification, the outlet tube 625 includes a unidirectional valve 650 for allowing the drug to flow towards the eye under low pressure gradient conditions and preventing retrograde flow back towards the membrane 610 and reservoir 645. In an embodiment, as shown in FIG. 6C, the unidirectional valve 650 is formed in a "wet straw" configuration where a generally circular cross-section 652 is drawn to a flattened end 654. With this configuration, a positive pressure gradient serves to open the "wet straw" to allow fluid to flow in the direction of the arrow 655, whereas a negative pressure gradient will cause valve 650 to collapse on itself to prevent retrograde flow. Because of its pliability and its low frictional properties, TEFLON (polytetrafluoroethylene) is a suitable material for the construction of valve 650, although other materials may be found to function satisfactorily.

In some embodiments, the plates 605, 620 are substantially rectangular with curved corners and have a length of 16.0 mm, a breadth of 13.0 mm, a thickness of 2.1 mm and a surface area of 184.0 mm$^2$. In embodiments, the outlet tube 625 is about 25.4 mm long, has an outer diameter of 0.635 mm and an inner diameter of 0.305 mm.

Figure 6D:
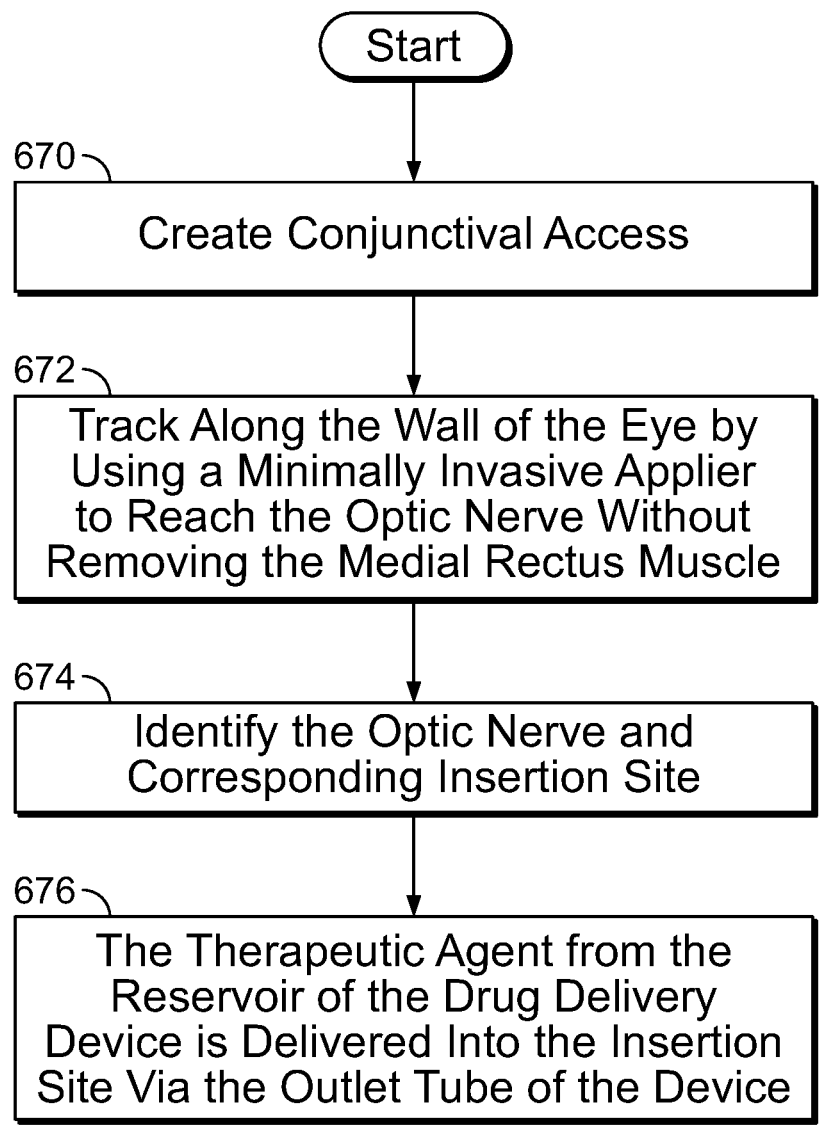
FIG. 6D is a flowchart illustrating a method of surgical implantation of the drug delivery device 600, in accordance with an embodiment of the present specification; and, FIG. 7 is a perspective view of a stent applicator or delivery system, in accordance with an embodiment of the present specification.

FIG. 6D is a flowchart illustrating a method of surgical implantation of the drug delivery device 600, in accordance with an embodiment of the present specification. At step 670, a conjunctival access is created in the patient's eye. In another embodiment, a small conjunctival incision is performed, avoiding a full peritomy, and the sclera of the eye is bared. At step 672, a minimally invasive applier, such as an endoscope with visualization and a curved distal end, is used to track along the wall of the eye to reach the optic nerve without the need for a significant abduction or reversion of the eyeball and thereby not requiring the medial rectus muscle to be removed. In an embodiment, a viscoelastic may injected between sclera and Tenon's capsule. In alternative embodiments, a fluid may be infused or irrigated through the optic nerve sheath for gentle visco-dissection of the sheath without the injection of a viscoelastic material. At step 674, a micro dissecting retractor or forceps is used to identify the optic nerve, and an insertion site is identified on the optic nerve. At step 676, the drug delivery device is inserted in to the optic nerve sheath at the site identified in the previous step. At step 678, the therapeutic agent from the reservoir of the drug delivery device is delivered into the insertion site via the outlet tube of the device.

The drug delivery device 600 and its implantation using the surgical method of FIG. 3A enable continuous delivery of drugs, such as analgesics (for pain management), anti-cancer drugs, antibiotics, neurologic related spasticity drugs, and other therapeutics that require drug delivery via cerebral spinal fluid such as for, but not limited to, intrathecal chemotherapy. Thus, the drug delivery device 600 enables delivery of drugs for treatment of a plurality of central nervous system diseases including, but not limited to, oncologic, infectious and immune diseases, where delivery of therapeutic agents into the CSF and the CNS is essential. In various embodiments, the therapeutics or drugs are either small or large molecules such as, but not limited to, antibiotics, chemotherapeutic agents and other biologics known to persons of ordinary skill in the art. Exemplary anti-cancer compositions include cisplatin, cetuximab, carboplatin cis-platinum, platamine, neoplatin, cismaplat, docetaxel, paclitaxel, and methotrexate.

The following are an examples of dosing regimens for any primary or secondary cancers: Use Case—Leptomeningeal Metastasis of tumors, such as, but not limited to, Gliomas, Melanoma, Breast, Lung, Lymphoma, Leukemia, Prostate, Testicular, Ovarian, Pancreatic, and GI tumors.

Current Treatment—Single medication or combination of medications such as, but not limited to, Methotrexate, Cytarabine, Hydrocortisone, and Thiotepa.

Dosage and Regimen—Given the reservoir and the ability to have a time-sensitive and sustained dosing (which could help with side effects related to the above medications), dosage and regimen vary based on the weight of the patient and type of tumor. For example, for Leptomeningeal spread from Lymphoma the following treatment regimen is followed:

| Drug | Dose | BCCA administration Guideline |
| --- | --- | --- |
| Methotrexate | 12 mg, on days 1, 8 and 15 | Intrathecal qs to 6 mL with preservative-free NS |
| Cytarabine | 50 mg on days 4, 11 and 18 | Intrathecal qs to 6 mL with preservative-free NS |

In another non-limiting use case, the reservoir 645 enables administering of therapeutics for elevated intracranial pressure (ICP), such as resulting from space travel, for example. In embodiments, the reservoir 645 delivers Diamox in a sustained dosing (such as, 250 milligram to 500 milligram orally, twice daily) to prevent optic disc edema and symptoms related to elevated ICP, such as transient visual obscurations, headaches, tinnitus, vertigo and double vision.

Delivery Apparatus/Applicator

In embodiments, an applicator is used to deploy the stent or the shunt. In an embodiment, the applicator (or applier) comprises viewing apparatus such as an endoscopic camera. In an embodiment, the applier has a curved configuration that may enable the applier to move along the wall of the eye in order to reach the optic nerve during the surgical procedure. The curved configuration may also enable access to the optic nerve without need for significant abduction/eversion of the eyeball, and thus may not require removal of medial rectus muscle.

In an embodiment, use of an endoscopic applier to deploy the stent may curb the need of a viscoelastic or any other fluid which is otherwise injected between the sclera and the Tenon's capsule.

Figure 7:
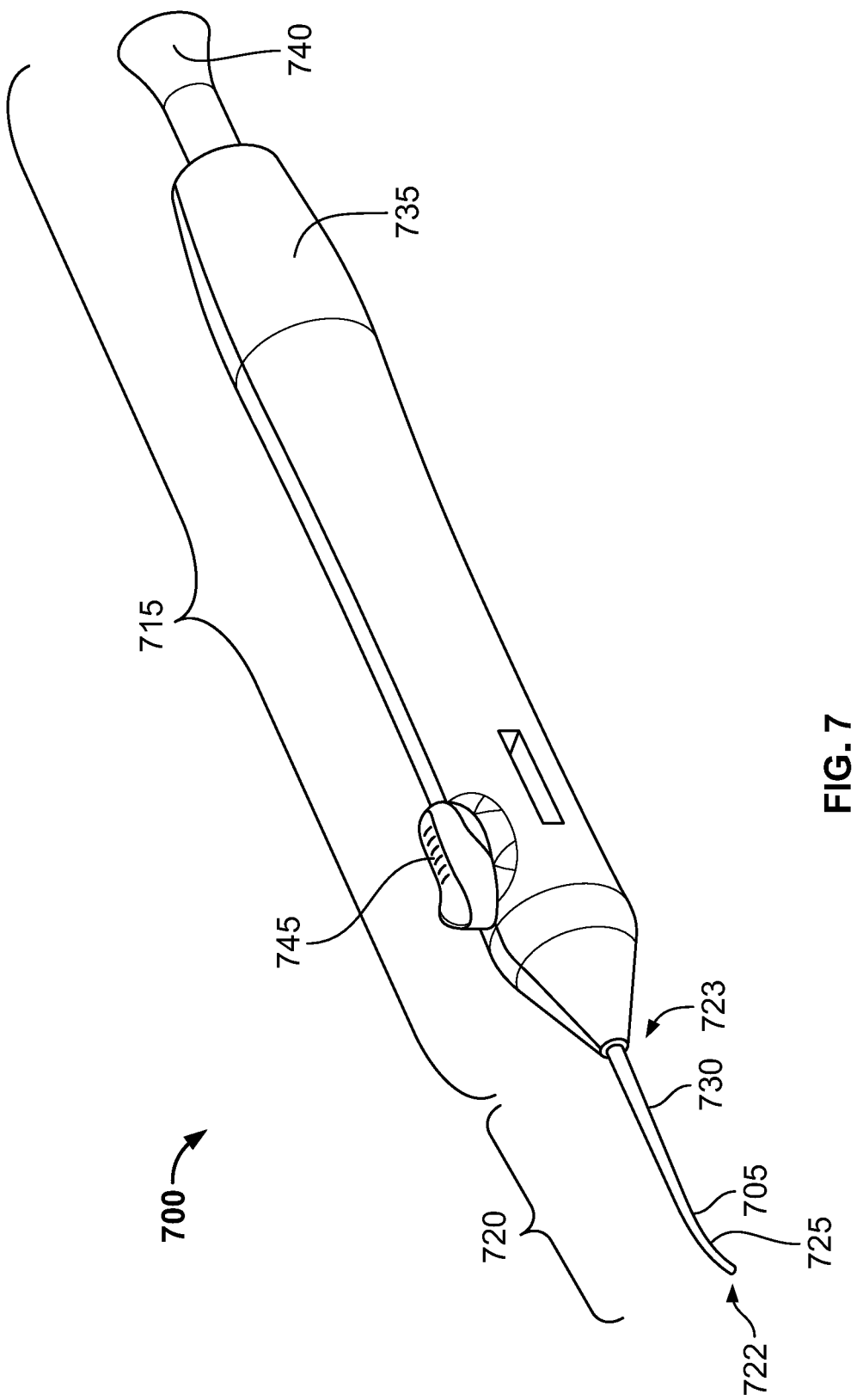

FIG. 7 is an exemplary applicator or delivery system 700, in accordance with an embodiment of the present specification, that can be used to deliver or implant a stent or shunt 705 (such as the stents or shunts 400a, 400b of FIGS. 4A, 4B respectively). The delivery system 700 comprises a handle portion 715 and a delivery portion 720 that may be removably coupled to the shunt 705 for delivery or implantation of the shunt 705 into an eye. The delivery portion 720 includes an elongate applier or guidewire 725 which may be curved or non-curved. The applier or guidewire 725 is sized to fit through the lumen of the shunt 705 such that the shunt 705 can be mounted on the applier 725. In various embodiments, the applier 725 has a cross-sectional shape that complements the cross-sectional shape of the internal lumen of the shunt 705 to facilitate mounting of the shunt onto the applier 725. In some embodiments, the applier 725 has a sharpened distal tip 722. In alternate embodiments, the applier 725 can have an atraumatic or blunt distal tip 722 such that it serves as a component for coupling to the shunt, or performing blunt dissection, rather than as a cutting element. In still alternate embodiments, the delivery portion 720 does not include a guidewire.

The delivery portion 720 also includes a shunt deployment or advancing element 730 positioned on a proximal end 723 of the applier 725. In some embodiments, the advancing element 730 is an elongated tube that is positioned over the applier 725. The delivery system 700 is actuated to achieve relative, sliding movement between the advancing element 730 and the applier 725. In embodiments, the advancing element 630 is moved in the distal direction, while the applier 725 remains stationary to push or otherwise advance the shunt 705 along the applier 725 for delivery of the shunt 705 into the eye. In an alternate embodiment, the applier 725 withdraws into the advancing element 730 to remove the shunt 705 from the applier 725. In yet another embodiment, both the advancing element 730 and the applier 725 move relative to one another to remove the shunt 705.

In an embodiment, the applier 725 has a length sufficient to receive a plurality of shunts in an end-to-end series arrangement on the applier 725. In this embodiment, plurality of shunts 705 can be loaded onto the applier 725 and implanted one at a time such that the shunts collectively form an elongated lumen of sufficient length for adequate drainage of aqueous humour. This allows relatively short length shunts that can be collectively used in various eye sizes.

The handle portion 715 is actuated to control delivery of the shunt 705. In embodiments, the handle portion 715 includes an applier or guidewire extension button 740 that is actuated to cause the applier or guidewire 725 to extend in length in the distal direction. In embodiments, the handle portion 715 includes an applier or guidewire retraction button 745 that is actuated to cause the applier or guidewire 725 to retract in length in the proximal direction. In some embodiments, the handle portion 715 also includes a shunt advancing actuator 735 that can be actuated to selectively move the advancing element 730 along the applier 725—in the proximal or distal direction. Using the actuator 735, the advancing element 730 can be used to push the shunt 705 in the distal direction and off of the applier 725 during delivery, or else to hold the shunt 705 in a fixed location in the eye while the applier 725 is withdrawn.

In some embodiments, the applier 725 passes through the conjunctiva to access the retrobulbar space of a subject and implants the stent or shunt 705 through the optical sheath. In other embodiments, the applier 725 passes through Tenon's, or any other part within the anatomy of the eye that allows access to the retrobulbar space.

In various embodiments, the applier or guidewire 725 can be straight or the applier 725 can be curved along all or a portion of its length, such as at the distal tip 722 (as shown in FIG. 7) in order to facilitate proper placement through the cornea. The curved configuration may also enable access to the optic nerve without need for significant abduction/eversion of the eyeball, and thus may not require removal of medial rectus muscle. Accordingly, the curvature of the applier 725 can vary. For example, the applier 725 can have a radius of curvature of 3 mm to 50 mm and the curve can cover from up to 180 degrees in various embodiments. In one embodiment, the applier 725 has a radius of curvature that corresponds to or complements the radius of curvature of a region of the eye, such as the suprachoroidal space.

In various embodiments, the system 700 is an endoscopic applicator wherein the handle portion 715 or the delivery portion 720 (such as the guidewire 725 or the shunt deployment or advancing element 730) comprises one or more illumination elements, such as LEDs (Light Emitting Diodes) and at least one endoscopic viewing element, such as a camera, for posterior visualization in the orbit. In some embodiments, use of an endoscopic applicator to deploy the stent may curb the need of a viscoelastic fluid or any other fluid which is otherwise injected between the sclera and Tenon's capsule. However, in alternate embodiments, the system 700 may use a viscoelastic fluid or any other fluid for irrigation, such as, through the guidewire 725.

The above examples are merely illustrative of the many applications of the system of present specification. Although only a few embodiments of the present specification have been described herein, it should be understood that the present specification might be embodied in many other specific forms without departing from the spirit or scope of the specification. For example, while the presently disclosed specifications are indicated to treat papilledema due to intracranial hypertension, they may also be employed to treat cases of papilledema with impending or progressive visual loss due to an unresectable central nervous system mass, an arteriovascular malformation of the vein of Galen, venous sinus thrombosis, cryptococcal meningitis, and obstruction of the cerebral venous system from a compressive lesion. Therefore, the present examples and embodiments are to be considered as illustrative and not restrictive, and the specification may be modified within the scope of the appended claims.

We claim:

1. A surgical method for treating at least one of intracranial hypertension and papilledema in a patient, comprising:
navigating an applier device with a curved distal end along a wall of an eye of the patient without removing a medial rectus muscle associated with said eye;
using the applier device, injecting a viscoelastic between the sclera of said eye and a Tenon's capsule associated with said eye;
using the applier device, inserting at least one stent into an optic nerve sheath associated with the eye with one end of the stent inside the optic nerve sheath and an opposing end of the stent maintaining an opening to an outside of the optic nerve sheath;
inspecting for an amount of fluid egress from the at least one stent; and
removing the viscoelastic using an aspirator.

2. The method of claim 1 further comprising creating a conjunctival access behind said eye.

3. The method of claim 2 comprising performing at least one of a medial peritomy on said eye prior to injecting said viscoelastic and a conjunctival incision on said eye prior to injecting said viscoelastic.

4. The method of claim 3, wherein the medial peritomy is performed in a direction from 12 o'clock to 6 o'clock.

5. The method of claim 2 comprising performing a conjunctival incision.

6. The method of claim 1 further comprising dissecting bluntly to bare the sclera prior to injecting said viscoelastic.

7. The method of claim 6, wherein the dissecting is performed with Westcott scissors.

8. The method of claim 1 further comprising isolating the medial rectus muscle prior to injecting said viscoelastic.

9. The method of claim 1 further comprising identifying an insertion site on an optic nerve associated with the eye.

10. The method of claim 9 wherein the insertion site is at a distance of at least 1.5 mm from a globe of said eye.

11. The method of claim 9 comprising inserting the at least one stent at the insertion site, wherein said insertion site is at least 1.5 mm posterior to the optic nerve.

12. The method of claim 1 comprising inserting the at least one stent having a length between 3 mm and 6 mm.

13. The method of claim 12 comprising inserting the at least one stent having a diameter of 6 mm or less.

14. The method of claim 1 wherein the at least one stent comprises material with properties that are a combination of one or more of: bio-degradable, heparin-coated, non-ferromagnetic Titanium, polyamide, super-elastic, bio-compatible, an alloy of Nickel-Titanium, rigid, flexible, expandable, and non-expandable.

15. The method of claim 1 wherein the at least one stent has as an elongated tube.

16. The method of claim 15 wherein the at least one stent has a flat structure.

17. The method of claim 1 wherein the at least one stent shaped is J shaped, wherein a longer side of the J-shaped stent is longitudinally placed within the optic nerve sheath, and wherein the curved, shorter side maintains an opening to an outside of said optic nerve sheath.

18. The method of claim 1 wherein the at least one stent further comprises one or more sensors.

19. The method of claim 1 wherein the at least one stent further comprises one or more therapeutic compositions.

* * * * *